United States Patent
Rao et al.

(10) Patent No.: US 10,772,721 B2
(45) Date of Patent: Sep. 15, 2020

(54) ACCOMMODATING INTRAOCULAR LENS

(71) Applicant: LensGen, Inc., Irvine, CA (US)

(72) Inventors: Ramgopal Rao, Irvine, CA (US); David Miller, Jamaica Plain, MA (US)

(73) Assignee: LensGen, Inc., Irvine, CA (US)

( * ) Notice: Subject to any disclaimer, the term of this patent is extended or adjusted under 35 U.S.C. 154(b) by 0 days.

(21) Appl. No.: 15/995,671

(22) Filed: Jun. 1, 2018

(65) Prior Publication Data
US 2019/0000612 A1    Jan. 3, 2019

Related U.S. Application Data

(63) Continuation of application No. 13/662,087, filed on Oct. 26, 2012, now abandoned, which is a
(Continued)

(51) Int. Cl.
*A61F 2/16*    (2006.01)

(52) U.S. Cl.
CPC .... *A61F 2/1635* (2013.01); *A61F 2002/1682* (2015.04); *A61F 2002/16901* (2015.04); *A61F 2250/0018* (2013.01)

(58) Field of Classification Search
CPC ............................ A61F 2/1613; A61F 2/1635
See application file for complete search history.

(56) References Cited

U.S. PATENT DOCUMENTS 4,032,502 A    6/1977 Lee et al.
4,373,218 A    2/1983 Schachar
(Continued)

FOREIGN PATENT DOCUMENTS

DE    20 2010 003217 U1    8/2011
EP    0356050 A1    2/1990
(Continued)

OTHER PUBLICATIONS

International Search Report and Written Opinion dated Jul. 14, 2011 for PCT/US2011/034197 in 7 pages.
(Continued)

*Primary Examiner* — Christopher D. Prone
*Assistant Examiner* — Christine L Nelson
(74) *Attorney, Agent, or Firm* — Knobbe, Martens, Olson & Bear LLP (57) ABSTRACT

An accommodating intraocular lens (IOL) device adapted for implantation in the lens capsule of a subject's eye. The IOL device includes an anterior refractive optical element and a membrane coupled to the refractive optical element. The anterior refractive optical element and the membrane define an enclosed cavity configured to contain a fluid. At least a portion of the membrane is configured to contact a posterior area of the lens capsule adjoining the vitreous body of the subject's eye. The fluid contained in the enclosed cavity exerts a deforming or displacing force on the anterior refractive optical element in response to an anterior force exerted on the membrane by the vitreous body. The IOL device may further include a haptic system to position the anterior refractive optical element and also to engage the zonules and ciliary muscles to provide additional means for accommodation.

15 Claims, 7 Drawing Sheets

Related U.S. Application Data continuation of application No. PCT/US2011/034197, filed on Apr. 27, 2011.

(60) Provisional application No. 61/343,386, filed on Apr. 27, 2010.

(56) References Cited

U.S. PATENT DOCUMENTS

| | | |
|---|---|---|
| 4,512,040 A | 4/1985 | McClure |
| 4,585,457 A | 4/1986 | Kalb |
| 4,676,791 A | 6/1987 | LeMaster et al. |
| 4,720,286 A | 1/1988 | Bailey et al. |
| 4,731,078 A | 3/1988 | Stoy et al. |
| 4,822,360 A | 4/1989 | Deacon |
| 4,842,601 A | 6/1989 | Smith |
| 4,882,368 A | 11/1989 | Elias et al. |
| 4,888,012 A | 12/1989 | Horn et al. |
| 4,892,543 A | 1/1990 | Turley |
| 4,932,966 A | 7/1990 | Christie et al. |
| 5,035,710 A | 7/1991 | Nakada et al. |
| 5,059,668 A | 10/1991 | Fukuda et al. |
| 5,074,876 A | 12/1991 | Kelman |
| 5,091,121 A | 2/1992 | Nakada et al. |
| 5,152,788 A | 10/1992 | Isaacson et al. |
| 5,167,883 A | 12/1992 | Takemasa et al. |
| 5,171,773 A | 12/1992 | Chaffe et al. |
| 5,227,447 A | 7/1993 | Sato et al. |
| 5,236,970 A | 8/1993 | Christ et al. |
| 5,264,522 A | 11/1993 | Mize et al. |
| 5,275,623 A | 1/1994 | Sarfarazi |
| 5,278,258 A | 1/1994 | Gerace et al. |
| 5,312,860 A | 5/1994 | Mize et al. |
| 5,326,506 A | 7/1994 | Vanderbilt |
| 5,336,487 A | 8/1994 | Refojo et al. |
| 5,443,506 A | 8/1995 | Garabet |
| 5,447,987 A | 9/1995 | Sato et al. |
| 5,489,302 A | 2/1996 | Skottun |
| 5,583,178 A | 12/1996 | Oxman et al. |
| 5,607,472 A | 3/1997 | Thompson |
| 5,665,794 A | 9/1997 | Maxson et al. |
| 5,854,310 A | 12/1998 | Maxson |
| 6,071,439 A | 6/2000 | Bawa et al. |
| 6,117,171 A | 9/2000 | Skottun |
| 6,197,057 B1 | 3/2001 | Peyman et al. |
| 6,361,561 B1 | 3/2002 | Huo et al. |
| 6,551,354 B1 | 4/2003 | Ghazizadeh et al. |
| 6,616,691 B1 | 9/2003 | Tran |
| 6,695,881 B2 | 2/2004 | Peng et al. |
| 6,730,123 B1 | 5/2004 | Klopotek |
| 6,836,374 B2 | 12/2004 | Esch et al. |
| 6,855,164 B2 | 2/2005 | Glazier |
| 6,858,040 B2 | 2/2005 | Nguyen et al. |
| 6,860,601 B2 | 3/2005 | Shadduck |
| 6,926,736 B2 | 8/2005 | Peng et al. |
| 6,930,838 B2 | 8/2005 | Schachar |
| 6,935,743 B2 | 8/2005 | Shadduck |
| 6,966,649 B2 | 11/2005 | Shadduck |
| 6,969,403 B2 | 11/2005 | Peng et al. |
| 7,041,134 B2 | 5/2006 | Nguyen et al. |
| 7,063,723 B2 | 6/2006 | Ran |
| 7,068,439 B2 | 6/2006 | Esch et al. |
| 7,122,053 B2 | 10/2006 | Esch |
| 7,150,760 B2 | 12/2006 | Zhang |
| 7,217,288 B2 | 5/2007 | Esch et al. |
| 7,220,279 B2 | 5/2007 | Nun |
| 7,223,288 B2 | 5/2007 | Zhang et al. |
| 7,226,478 B2 | 6/2007 | Ting et al. |
| 7,229,475 B2 | 6/2007 | Glazier |
| 7,238,201 B2 | 7/2007 | Portney et al. |
| 7,247,168 B2 | 7/2007 | Esch et al. |
| 7,261,737 B2 | 8/2007 | Esch et al. |
| 7,264,351 B2 | 9/2007 | Shadduck |
| 7,276,619 B2 | 10/2007 | Kunzler et al. |
| 7,278,739 B2 | 10/2007 | Shadduck |
| 7,316,713 B2 | 1/2008 | Zhang |
| 7,416,562 B2 | 8/2008 | Gross |
| 7,438,723 B2 | 10/2008 | Esch |
| 7,452,377 B2 | 11/2008 | Watling et al. |
| 7,453,646 B2 | 11/2008 | Lo |
| 7,485,144 B2 | 2/2009 | Esch |
| 7,591,849 B2 | 9/2009 | Richardson |
| 7,637,947 B2 | 12/2009 | Smith et al. |
| 7,662,179 B2 | 2/2010 | Sarfarazi |
| 7,675,686 B2 | 3/2010 | Lo et al. |
| 7,753,953 B1 | 7/2010 | Yee |
| 7,776,088 B2 | 8/2010 | Shadduck |
| 7,780,729 B2 | 8/2010 | Nguyen et al. |
| 7,815,678 B2 | 10/2010 | Nun |
| 7,842,087 B2 | 11/2010 | Nun |
| 7,854,764 B2 | 12/2010 | Nun |
| 7,857,850 B2 | 12/2010 | Mentak et al. |
| 7,981,155 B2 | 7/2011 | Cumming |
| 7,985,253 B2 | 7/2011 | Cumming |
| 7,986,465 B1 | 7/2011 | Lo et al. |
| 7,998,198 B2 | 8/2011 | Angelopoulos et al. |
| 7,998,199 B2 | 8/2011 | Nun |
| 8,012,204 B2 | 9/2011 | Weinschenk, III et al. |
| 8,018,658 B2 | 9/2011 | Lo |
| 8,034,106 B2 | 10/2011 | Mentak et al. |
| 8,034,107 B2 | 10/2011 | Stenger |
| 8,038,711 B2 | 10/2011 | Clarke |
| 8,048,155 B2 | 11/2011 | Shadduck |
| 8,052,752 B2 | 11/2011 | Woods et al. |
| 8,062,361 B2 | 11/2011 | Nguyen et al. |
| 8,070,806 B2 | 12/2011 | Khoury |
| 8,158,712 B2 | 4/2012 | Your |
| 8,182,531 B2 | 5/2012 | Hermans et al. |
| 8,187,325 B2 | 5/2012 | Zadno-Azizi et al. |
| 8,197,541 B2 | 6/2012 | Schedler |
| 8,216,306 B2 | 7/2012 | Coroneo |
| 8,246,679 B2 | 8/2012 | Nguyen et al. |
| 8,254,034 B1 | 8/2012 | Shields et al. |
| 8,257,827 B1 | 9/2012 | Shi et al. |
| 8,273,123 B2 | 9/2012 | Nun |
| 8,303,656 B2 | 11/2012 | Shadduck |
| 8,314,927 B2 | 11/2012 | Choi et al. |
| 8,320,049 B2 | 11/2012 | Huang et al. |
| 8,328,869 B2 | 12/2012 | Smiley et al. |
| 8,361,145 B2 | 1/2013 | Scholl et al. |
| 8,377,124 B2 | 2/2013 | Hong et al. |
| 8,398,709 B2 | 3/2013 | Nun |
| 8,414,646 B2 | 4/2013 | De Juan, Jr. et al. |
| 8,425,597 B2 | 4/2013 | Glick et al. |
| 8,425,599 B2 | 4/2013 | Shadduck |
| 8,430,928 B2 | 4/2013 | Liao |
| 8,447,086 B2 | 5/2013 | Hildebrand et al. |
| 8,454,688 B2 | 6/2013 | Esch et al. |
| 8,475,529 B2 | 7/2013 | Clarke |
| 8,496,701 B2 | 7/2013 | Hermans et al. |
| 8,500,806 B1 | 8/2013 | Phillips |
| 8,545,556 B2 | 10/2013 | Woods et al. |
| 8,579,972 B2 | 11/2013 | Rombach |
| 8,585,758 B2 | 11/2013 | Woods |
| 8,608,799 B2 | 12/2013 | Blake |
| 8,608,800 B2 | 12/2013 | Portney |
| 8,613,766 B2 | 12/2013 | Richardson et al. |
| 8,647,384 B2 | 2/2014 | Lu |
| 8,657,878 B2 | 2/2014 | Mentak et al. |
| 8,668,734 B2 | 3/2014 | Hildebrand et al. |
| 8,690,942 B2 | 3/2014 | Hildebrand et al. |
| 8,715,345 B2 | 5/2014 | DeBoer et al. |
| 8,715,346 B2 | 5/2014 | De Juan, Jr. et al. |
| 8,734,509 B2 | 5/2014 | Mentak et al. |
| 8,771,347 B2 | 7/2014 | DeBoer et al. |
| 8,814,934 B2 | 8/2014 | Geraghty et al. |
| 8,834,565 B2 | 9/2014 | Nun |
| 8,858,626 B2 | 10/2014 | Noy |
| 8,867,141 B2 | 10/2014 | Pugh et al. |
| 8,900,298 B2 | 12/2014 | Anvar et al. |
| 8,900,300 B1 | 12/2014 | Wortz |
| 8,956,408 B2 | 2/2015 | Smiley et al. |
| 8,968,396 B2 | 3/2015 | Matthews et al. |
| 8,968,399 B2 | 3/2015 | Ghabra |
| 8,992,609 B2 | 3/2015 | Shadduck |

(56) References Cited

U.S. PATENT DOCUMENTS

| | | |
|---|---|---|
| 9,005,282 B2 | 4/2015 | Chang et al. |
| 9,005,283 B2 | 4/2015 | Nguyen et al. |
| 9,034,035 B2 | 5/2015 | Betser et al. |
| 9,044,317 B2 | 6/2015 | Hildebrand et al. |
| 9,072,600 B2 | 7/2015 | Tran |
| 9,090,033 B2 | 7/2015 | Carson et al. |
| 9,095,424 B2 | 8/2015 | Kahook et al. |
| 9,125,736 B2 | 9/2015 | Kahook et al. |
| 9,186,244 B2 | 11/2015 | Silvestrini et al. |
| 9,198,752 B2 | 12/2015 | Woods |
| 9,277,987 B2 | 3/2016 | Smiley et al. |
| 9,277,988 B1 | 3/2016 | Chu |
| 9,289,287 B2 | 3/2016 | Kahook et al. |
| 9,326,846 B2 | 5/2016 | Devita Gerardi et al. |
| 9,333,072 B2 | 5/2016 | Ichikawa |
| 9,358,103 B1 | 6/2016 | Wortz et al. |
| 9,364,316 B1 | 6/2016 | Kahook et al. |
| 9,387,069 B2 | 7/2016 | Kahook et al. |
| 9,421,088 B1 | 8/2016 | Kahook et al. |
| 9,427,312 B2 | 8/2016 | DeBoer et al. |
| 9,433,497 B2 | 9/2016 | DeBoer et al. |
| 9,456,895 B2 | 10/2016 | Shadduck |
| 9,486,311 B2 | 11/2016 | Argento et al. |
| 9,610,155 B2 | 4/2017 | Matthews |
| 9,622,852 B2 | 4/2017 | Simonov et al. |
| 9,629,712 B2 | 4/2017 | Stenger |
| 9,636,213 B2 | 5/2017 | Brady |
| 9,655,716 B2 | 5/2017 | Cumming |
| 9,681,946 B2 | 6/2017 | Kahook et al. |
| 9,693,858 B2 | 7/2017 | Hildebrand et al. |
| 9,713,526 B2 | 7/2017 | Rombach |
| 9,713,527 B2 | 7/2017 | Nishi et al. |
| 9,717,589 B2 | 8/2017 | Simonov et al. |
| 9,744,027 B2 | 8/2017 | Jansen |
| 9,744,028 B2 | 8/2017 | Simonov et al. |
| 9,795,473 B2 | 10/2017 | Smiley et al. |
| 9,808,339 B2 | 11/2017 | Dorronsoro Diaz et al. |
| 9,814,568 B2 | 11/2017 | Ben Nun |
| 9,814,570 B2 | 11/2017 | Robert et al. |
| 9,820,849 B2 | 11/2017 | Jansen |
| 9,848,980 B2 | 12/2017 | McCafferty |
| 9,855,137 B2 | 1/2018 | Smiley et al. |
| 9,855,139 B2 | 1/2018 | Matthews et al. |
| 9,861,469 B2 | 1/2018 | Simonov et al. |
| 9,872,762 B2 | 1/2018 | Scholl et al. |
| 9,872,763 B2 | 1/2018 | Smiley et al. |
| 9,877,825 B2 | 1/2018 | Kahook et al. |
| 9,883,940 B2 | 2/2018 | Nishi et al. |
| 9,925,039 B2 | 3/2018 | Sohn et al. |
| 9,925,040 B2 | 3/2018 | Kahook et al. |
| 9,931,202 B2 | 4/2018 | Borja et al. |
| 9,987,126 B2 | 6/2018 | Borja et al. |
| 10,004,596 B2 | 6/2018 | Brady et al. |
| 10,028,824 B2 | 7/2018 | Kahook et al. |
| 10,045,844 B2 | 8/2018 | Smiley et al. |
| 10,080,648 B2 | 9/2018 | Kahook et al. |
| 10,111,745 B2 | 10/2018 | Silvestrini et al. |
| 10,159,564 B2 | 12/2018 | Brady et al. |
| 10,195,018 B2 | 2/2019 | Salahieh et al. |
| 10,195,020 B2 | 2/2019 | Matthews |
| 10,526,353 B2 | 1/2020 | Silvestrini |
| 2002/0005344 A1 | 1/2002 | Heidlas et al. |
| 2002/0055776 A1 | 5/2002 | Juan, Jr. et al. |
| 2002/0071856 A1 | 6/2002 | Dillingham et al. |
| 2002/0120329 A1 | 8/2002 | Lang et al. |
| 2003/0093149 A1 | 5/2003 | Glazier |
| 2003/0105522 A1 | 6/2003 | Glazier |
| 2003/0109926 A1 | 6/2003 | Portney |
| 2003/0158295 A1 | 8/2003 | Fukuda et al. |
| 2004/0082993 A1 | 4/2004 | Woods |
| 2004/0082994 A1 | 4/2004 | Woods et al. |
| 2004/0111152 A1 | 6/2004 | Kelman |
| 2004/0148023 A1 | 7/2004 | Shu |
| 2004/0162612 A1 | 8/2004 | Portney et al. |
| 2004/0169816 A1 | 9/2004 | Esch |
| 2004/0249455 A1 | 12/2004 | Tran |
| 2005/0021139 A1 | 1/2005 | Shadduck |
| 2005/0071002 A1 | 3/2005 | Glazier |
| 2005/0107873 A1 | 5/2005 | Zhou |
| 2005/0137703 A1 | 6/2005 | Chen |
| 2005/0251253 A1 | 11/2005 | Gross |
| 2005/0251254 A1 | 11/2005 | Brady et al. |
| 2005/0267575 A1 | 12/2005 | Nguyen et al. |
| 2006/0041307 A1 | 2/2006 | Esch et al. |
| 2006/0047339 A1 | 3/2006 | Brown |
| 2006/0069178 A1 | 3/2006 | Rastogi et al. |
| 2006/0074487 A1 | 4/2006 | Gilg |
| 2006/0111776 A1 | 5/2006 | Glick et al. |
| 2006/0134173 A1 | 6/2006 | Liu et al. |
| 2006/0135477 A1 | 6/2006 | Haitjema et al. |
| 2006/0212116 A1 | 9/2006 | Woods |
| 2006/0238702 A1 | 10/2006 | Glick et al. |
| 2006/0241752 A1 | 10/2006 | Israel |
| 2007/0016293 A1 | 1/2007 | Tran |
| 2007/0032868 A1 | 2/2007 | Woods et al. |
| 2007/0050024 A1 | 3/2007 | Zhang |
| 2007/0050025 A1 | 3/2007 | Nguyen et al. |
| 2007/0078515 A1 | 4/2007 | Brady et al. |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0118216 A1 | 5/2007 | Pynson |
| 2007/0129798 A1 | 6/2007 | Chawdhary |
| 2007/0129799 A1 | 6/2007 | Schedler |
| 2007/0129800 A1 | 6/2007 | Cumming |
| 2007/0129801 A1 | 6/2007 | Cumming |
| 2007/0132949 A1 | 6/2007 | Phelan |
| 2007/0213817 A1 | 9/2007 | Esch et al. |
| 2007/0260308 A1 | 11/2007 | Tran |
| 2007/0260310 A1 | 11/2007 | Richardson |
| 2008/0015689 A1 | 1/2008 | Esch et al. |
| 2008/0033547 A1 | 2/2008 | Chang et al. |
| 2008/0046074 A1 | 2/2008 | Smith et al. |
| 2008/0046075 A1 | 2/2008 | Esch et al. |
| 2008/0046077 A1 | 2/2008 | Cumming |
| 2008/0051886 A1 | 2/2008 | Lin |
| 2008/0154364 A1 | 6/2008 | Richardson et al. |
| 2008/0200982 A1 | 8/2008 | Your |
| 2008/0269887 A1 | 10/2008 | Cumming |
| 2008/0300680 A1 | 12/2008 | Nun |
| 2008/0306587 A1 | 12/2008 | Your |
| 2008/0306588 A1 | 12/2008 | Smiley et al. |
| 2008/0306589 A1 | 12/2008 | Donitzky et al. |
| 2009/0005865 A1 | 1/2009 | Smiley et al. |
| 2009/0027661 A1 | 1/2009 | Choi et al. |
| 2009/0043384 A1 | 2/2009 | Niwa et al. |
| 2009/0116118 A1 | 5/2009 | Frazier et al. |
| 2009/0125106 A1 | 5/2009 | Weinschenk, III et al. |
| 2009/0149952 A1 | 6/2009 | Shadduck |
| 2009/0198326 A1 | 8/2009 | Zhou et al. |
| 2009/0204209 A1 | 8/2009 | Tran |
| 2009/0204210 A1 | 8/2009 | Pynson |
| 2009/0264998 A1* | 10/2009 | Mentak ............... A61F 2/1613 623/6.37 |
| 2009/0292355 A1 | 11/2009 | Boyd et al. |
| 2009/0319040 A1* | 12/2009 | Khoury ............... A61F 2/1635 623/6.13 |
| 2010/0004742 A1 | 1/2010 | Cumming |
| 2010/0055449 A1 | 3/2010 | Ota |
| 2010/0057095 A1 | 3/2010 | Khuray et al. |
| 2010/0094412 A1 | 4/2010 | Wensrich |
| 2010/0094413 A1 | 4/2010 | Rombach et al. |
| 2010/0131058 A1 | 5/2010 | Shadduck |
| 2010/0131059 A1 | 5/2010 | Callahan et al. |
| 2010/0179653 A1 | 7/2010 | Argento et al. |
| 2010/0204787 A1 | 8/2010 | Noy |
| 2010/0211169 A1 | 8/2010 | Stanley et al. |
| 2010/0228344 A1 | 9/2010 | Shadduck |
| 2010/0288346 A1 | 9/2010 | Esch |
| 2010/0324672 A1 | 12/2010 | Esch et al. |
| 2010/0324674 A1 | 12/2010 | Brown |
| 2011/0029074 A1 | 2/2011 | Reisin et al. |
| 2011/0071628 A1 | 3/2011 | Gross et al. |
| 2011/0118834 A1 | 5/2011 | Lo et al. |

(56) References Cited

U.S. PATENT DOCUMENTS

| | | |
|---|---|---|
| 2011/0118836 A1 | 5/2011 | Jain |
| 2011/0208301 A1 | 8/2011 | Anvar et al. |
| 2011/0224788 A1* | 9/2011 | Webb ............ A61F 2/14 623/6.43 |
| 2011/0282442 A1 | 11/2011 | Scholl et al. |
| 2011/0288638 A1 | 11/2011 | Smiley et al. |
| 2012/0016473 A1 | 1/2012 | Brady et al. |
| 2012/0035724 A1 | 2/2012 | Clarke |
| 2012/0071972 A1 | 3/2012 | Zhao |
| 2012/0078364 A1 | 3/2012 | Stenger |
| 2012/0095125 A1 | 4/2012 | Hu et al. |
| 2012/0232649 A1 | 9/2012 | Cuevas |
| 2012/0245683 A1 | 9/2012 | Christie et al. |
| 2012/0253458 A1 | 10/2012 | Geraghty et al. |
| 2012/0253459 A1 | 10/2012 | Reich et al. |
| 2012/0290084 A1 | 11/2012 | Coroneo |
| 2012/0296423 A1 | 11/2012 | Caffey |
| 2012/0296424 A1 | 11/2012 | Betser |
| 2012/0310341 A1 | 12/2012 | Simonov et al. |
| 2012/0310343 A1 | 12/2012 | Van Noy |
| 2013/0006353 A1 | 1/2013 | Betser et al. |
| 2013/0035760 A1 | 2/2013 | Portney |
| 2013/0038944 A1 | 2/2013 | Chang et al. |
| 2013/0060331 A1 | 3/2013 | Shadduck |
| 2013/0110234 A1 | 5/2013 | DeVita et al. |
| 2013/0110235 A1 | 5/2013 | Shweigerling |
| 2013/0116781 A1 | 5/2013 | Nun |
| 2013/0131794 A1 | 5/2013 | Smiley et al. |
| 2013/0190867 A1 | 7/2013 | Peyman |
| 2013/0231741 A1 | 9/2013 | Clarke |
| 2013/0250239 A1 | 9/2013 | Hildebrand et al. |
| 2013/0268070 A1 | 10/2013 | Esch et al. |
| 2013/0297018 A1 | 11/2013 | Brady et al. |
| 2013/0317607 A1 | 11/2013 | DeBoer et al. |
| 2013/0317608 A1 | 11/2013 | Hermans et al. |
| 2014/0012277 A1 | 1/2014 | Matthews et al. |
| 2014/0058507 A1 | 2/2014 | Reich et al. |
| 2014/0085726 A1 | 3/2014 | Portney |
| 2014/0100654 A1 | 4/2014 | Portney et al. |
| 2014/0107459 A1 | 4/2014 | Lind et al. |
| 2014/0111765 A1 | 4/2014 | DeBoer et al. |
| 2014/0121768 A1 | 5/2014 | Simpson |
| 2014/0135917 A1 | 5/2014 | Glazier |
| 2014/0135918 A1 | 5/2014 | De Juan, Jr. et al. |
| 2014/0142558 A1 | 5/2014 | Culbertson et al. |
| 2014/0172092 A1 | 6/2014 | Carson et al. |
| 2014/0180404 A1 | 6/2014 | Tram |
| 2014/0180405 A1 | 6/2014 | Weinschenk, III et al. |
| 2014/0180406 A1 | 6/2014 | Simpson |
| 2014/0180407 A1 | 6/2014 | Sohn et al. |
| 2014/0180410 A1 | 6/2014 | Gerardi |
| 2014/0227437 A1 | 8/2014 | DeBoer et al. |
| 2014/0228949 A1 | 8/2014 | Argento et al. |
| 2014/0249625 A1 | 9/2014 | Shadduck |
| 2014/0257478 A1 | 9/2014 | McCafferty |
| 2014/0257479 A1 | 9/2014 | McCafferty |
| 2014/0309734 A1 | 10/2014 | Sohn et al. |
| 2015/0087743 A1 | 3/2015 | Anvar et al. |
| 2015/0105760 A1 | 4/2015 | Rao et al. |
| 2015/0127102 A1 | 5/2015 | Wortz |
| 2015/0173892 A1 | 6/2015 | Borja et al. |
| 2015/0202041 A1 | 7/2015 | Shadduck |
| 2015/0216652 A1 | 8/2015 | Jansen |
| 2015/0238310 A1 | 8/2015 | Matthews et al. |
| 2015/0366656 A1 | 12/2015 | Wortz et al. |
| 2016/0000558 A1 | 1/2016 | Honigsbaum |
| 2016/0008126 A1 | 1/2016 | Salahieh et al. |
| 2016/0051361 A1 | 2/2016 | Phillips |
| 2016/0058553 A1 | 3/2016 | Salahieh et al. |
| 2016/0074154 A1 | 3/2016 | Woods |
| 2016/0184089 A1 | 6/2016 | Dudee et al. |
| 2016/0184092 A1 | 6/2016 | Smiley et al. |
| 2016/0208138 A1 | 7/2016 | Nishijima et al. |
| 2016/0256265 A1 | 9/2016 | Borja et al. |
| 2016/0262875 A1 | 9/2016 | Smith et al. |
| 2016/0281019 A1 | 9/2016 | Deklippel et al. |
| 2016/0287380 A1 | 10/2016 | Shi et al. |
| 2016/0317287 A1 | 11/2016 | Silvestrini et al. |
| 2017/0020662 A1 | 1/2017 | Shadduck |
| 2017/0049561 A1 | 2/2017 | Smiley et al. |
| 2017/0049562 A1 | 2/2017 | Argento et al. |
| 2017/0216021 A1 | 8/2017 | Brady |
| 2017/0247525 A1 | 8/2017 | Silverstrini et al. |
| 2017/0290658 A1 | 10/2017 | Hildebrand et al. |
| 2017/0319332 A1 | 11/2017 | Kahook et al. |
| 2017/0342096 A1 | 11/2017 | Silvestrini |
| 2017/0348095 A1 | 12/2017 | Wortz et al. |
| 2018/0014928 A1 | 1/2018 | Kahook et al. |
| 2018/0028308 A1 | 2/2018 | Smiley et al. |
| 2018/0110613 A1 | 4/2018 | Wortz et al. |
| 2018/0125640 A1 | 5/2018 | Smiley et al. |
| 2018/0132997 A1 | 5/2018 | Smiley et al. |
| 2018/0147051 A1 | 5/2018 | Scholl et al. |
| 2018/0153682 A1 | 6/2018 | Hajela et al. |
| 2018/0161152 A1 | 6/2018 | Argento et al. |
| 2018/0161153 A1 | 6/2018 | Kahook et al. |
| 2018/0177589 A1 | 6/2018 | Argento et al. |
| 2018/0177639 A1 | 6/2018 | Rao et al. |
| 2018/0256315 A1 | 9/2018 | Hildebrand et al. |
| 2018/0271642 A1 | 9/2018 | Wortz et al. |
| 2018/0271645 A1 | 9/2018 | Brady et al. |
| 2018/0280135 A1 | 10/2018 | Otts |
| 2018/0296323 A1 | 10/2018 | Olcina Portilla |
| 2018/0307061 A1 | 10/2018 | State et al. |
| 2018/0318068 A1 | 11/2018 | Otts et al. |
| 2018/0344453 A1 | 12/2018 | Brady |
| 2018/0368971 A1 | 12/2018 | Zacher et al. |
| 2018/0368973 A1 | 12/2018 | Wortz et al. |
| 2018/0368974 A1 | 12/2018 | Kahook et al. |
| 2019/0015198 A1 | 1/2019 | Kuiper |
| 2019/0021848 A1 | 1/2019 | Kahook et al. |
| 2019/0069989 A1 | 3/2019 | Otts et al. |
| 2019/0076239 A1 | 3/2019 | Wortz et al. |
| 2019/0076243 A1 | 3/2019 | Hadba et al. |
| 2019/0083235 A1 | 3/2019 | Wortz |
| 2019/0099263 A1 | 4/2019 | Brady et al. |
| 2019/0374334 A1 | 12/2019 | Brady et al. |

FOREIGN PATENT DOCUMENTS

| | | |
|---|---|---|
| EP | 0766540 B1 | 8/1999 |
| EP | 1881818 B1 | 7/2015 |
| JP | H09-150002 A | 6/1997 |
| JP | 2005-511201 | 4/2005 |
| JP | 2006-511245 | 4/2006 |
| JP | 2006-516002 | 6/2006 |
| JP | 2010-514507 | 5/2010 |
| JP | 2013-047290 | 3/2013 |
| WO | WO 92/17132 | 10/1992 |
| WO | WO 99/29266 | 6/1999 |
| WO | WO 2001/034067 | 5/2001 |
| WO | WO 2004/037127 | 5/2004 |
| WO | WO 2004/052242 | 6/2004 |
| WO | WO 2004/054471 | 7/2004 |
| WO | WO 2004/072689 | 8/2004 |
| WO | WO 2006/047383 | 5/2006 |
| WO | WO 2007/005778 | 1/2007 |
| WO | WO 2007/047529 | 4/2007 |
| WO | WO 2007/047530 | 4/2007 |
| WO | WO 2008/024766 | 2/2008 |
| WO | WO 2008/031231 | 3/2008 |
| WO | WO 2008/077040 | 6/2008 |
| WO | WO 2008/082957 | 7/2008 |
| WO | WO 2008/103798 | 8/2008 |
| WO | WO 2009/015161 | 1/2009 |
| WO | WO 2009/015226 | 1/2009 |
| WO | WO 2009/015234 | 1/2009 |
| WO | WO 2009/015240 | 1/2009 |
| WO | WO 2009/064876 | 5/2009 |
| WO | WO 2010/010565 | 1/2010 |
| WO | WO 2010/081093 | 7/2010 |
| WO | WO 2011/026068 | 3/2011 |
| WO | WO 2011/106435 | 9/2011 |
| WO | WO 2011/137191 | 11/2011 |

(56) References Cited

FOREIGN PATENT DOCUMENTS

| WO | WO 2012/006616 | 1/2012 |
|---|---|---|
| WO | WO 2012/129407 | 9/2012 |
| WO | WO 2013/016804 | 2/2013 |
| WO | WO 2013/070924 | 5/2013 |
| WO | WO 2013/142323 | 9/2013 |
| WO | WO 2013/166068 | 11/2013 |
| WO | WO 2013/180254 | 12/2013 |
| WO | WO 2013/190130 | 12/2013 |
| WO | WO 2014/099630 | 6/2014 |
| WO | WO 2014/145562 | 9/2014 |
| WO | WO 2014/152017 | 9/2014 |
| WO | WO 2014/197170 | 12/2014 |
| WO | WO 2015/066502 | 5/2015 |
| WO | WO 2015/066532 | 5/2015 |
| WO | WO 2015/126604 | 8/2015 |
| WO | WO 2016/018932 | 2/2016 |
| WO | WO 2016/033217 | 3/2016 |
| WO | WO 2016/122805 | 8/2016 |
| WO | WO 2016/201351 | 12/2016 |
| WO | WO 2017/079449 | 5/2017 |
| WO | WO 2017/079733 | 5/2017 |
| WO | WO 2017/087358 | 5/2017 |
| WO | WO 2017/096087 | 6/2017 |
| WO | WO 2017/192855 | 11/2017 |
| WO | WO 2018/081595 | 5/2018 |
| WO | WO 2018/119408 | 6/2018 |
| WO | WO 2018/167099 | 9/2018 |
| WO | WO 2018/222579 | 12/2018 |
| WO | WO 2018/227014 | 12/2018 |
| WO | WO 2019/005859 | 1/2019 |
| WO | WO 2019/027845 | 2/2019 |

OTHER PUBLICATIONS

Ehrmann, et al., "Biomechanical analysis of the accommodative apparatus in primates", Clinical and Experimental Optometry, May 2008, vol. 91, Issue 3, pp. 302-312.

Ehrmann, et al., "Ex Vivo Accommodation Simulator II—Concept and Preliminary Results", Proceedings of SPIE vol. 5314, Ophthalmic Technologies XIV, Jul. 2004, pp. 48-58.

Gabel, et al., "Silicone oil with high specific gravity for intraocular use", British Journal of Ophthalmology, Apr. 1987, vol. 71, 262-267.

Ghallagher-Wetmore, et al., "Supercritical fluid processing: a new dry technique for photoresist developing", SPIE's 1995 Symposium on Microlithography, 1995, vol. 2438, 16 pages.

Lane, et al., "Comparison of the biomechanical behavior of foldable intraocular lenses", Journal of Cataract Refract Surg, Nov. 2004, vol. 30, pp. 2397-2402.

Nakamura, et al., "Analysis and Fractionation of Silicone and Fluorosilicone Oils for Intraocular Use", Investigative Ophthalmology & Visual Science, vol. 31, No. 10, Oct. 1990, 2059-2069.

National Center for Biotechnology Information. PubChem Substance Database; SID=184590955, https://pubchem.ncbi.nlm.nih.gov/substance/184590955 (accessed Sep. 20, 2017).

Zhang, et al., "Fluidic adaptive lens with high focal length tunability", Applied Physics Letters, May 2003, vol. 82, No. 19, pp. 3171-3172.

Zhang, et al., "Integrated fluidic adaptive zoom lens", Optics Letters, Dec. 2004, vol. 29, No. 24, pp. 2855-2857.

Zhao, et al., "Strategies for Supercritical $CO_2$ Fractionation of Polydimethylsiloxane," Journal of Applied Polymer Science, 1995, vol. 55, 773-778.

\* cited by examiner

ACCOMMODATING INTRAOCULAR LENS

CROSS REFERENCE TO RELATED APPLICATIONS

The present application is a continuation of U.S. patent application Ser. No. 13/662,087, filed on Oct. 26, 2012, which is a continuation of International Application No. PCT/US2011/034197, filed Apr. 27, 2011, which in turn claims the benefit of U.S. Provisional Application No. 61/343,386, filed Apr. 27, 2010, the contents of which are incorporated herein by reference in their entireties into the present disclosure.

FIELD OF THE INVENTION

The invention relates generally to an accommodating intraocular lens device and, more particularly, to an accommodating intraocular lens device configured for implantation in a lens capsule of a subject's eye.

BACKGROUND

A cataract is a clouding of the lens in the eye that affects vision. While most cataracts are related to aging, cataracts may also develop as a result of traumatic eye injury, glaucoma, diabetes, steroid use, and exposure to radiation, to name a few. If left untreated, cataracts progress to eventual vision loss and even complete blindness.

Cataracts are typically treated by surgically removing the clouded lens matrix and implanting a replacement artificial intraocular lens (IOL) in the lens capsule that remains. The first generation of implanted IOL devices comprised monofocal lenses, which provided vision correction at only a single distance. Thus, while monofocal lenses provided distance vision, corrective lenses were still required for reading.

Multifocal lenses for IOL devices were introduced to provide vision correction at more than one distance with the goal of obviating the need for additional corrective lenses required with the monofocal lenses. Multifocal lenses typically have areas of varying refractive power to provide vision at multiple distances (e.g., near, intermediate and far). One significant disadvantage to multi focal lenses is the possibility of visual distortions, particularly in the form of glare and halos around light sources at night.

Accommodating IOL devices have recently been introduced as yet another alternative IOL for use in cataract surgery. Accommodating IOL devices typically feature a monofocal lens that is configured to move forward and backward within the eye in response to the eye's natural mechanism of accommodation, thereby allowing the eye to focus on objects across a broad range of distances. Currently, Crystalens® by Bausch and Lomb is the only FDA-approved accommodating IOL on the market in the United States. This device comprises a relatively flat central lens and a pair hinged haptics protruding from the central lens. The haptics respond to the contraction and relaxation of the eye's ciliary muscles to move the central lens portion forward and backward within the eye to provide varying dioptres of power. The Crystalens® device relies solely on the eye's ciliary muscle function in order to provide accommodation. Moreover, because the profile of the Crystalens® device is substantially smaller than that of the natural lens capsule, implantation of this device is followed by shrinkage of the natural lens capsule about the device. As the natural lens capsule shrinks, the zonules are further stretched away from the ciliary muscles, with the attendant loss of the eye's accommodative range.

Dual-lens IOL devices have been developed with the goal of providing a broader range of accommodation that is closer to the eye's natural range. The dual-lens IOL devices typically feature an anterior and a posterior lens in a spaced relation and rely solely on the ciliary muscles to actuate the anterior and posterior lens closer or farther together to alter the distance between them. The varying distance between the anterior and posterior lens provides the accommodation. Examples of dual-lens IOL devices include U.S. Pat. No. 5,275,623, issued to Sarfarazi on Jan. 4, 1994 and U.S. Pub. No. 2006/0178741 to Zadno-Azizi et al., published on Aug. 10, 2006. Dual-lens IOL devices generally suffer the disadvantage of being more complicated in design and requiring larger incisions in the eye for implantation. While the dual-lens IOL devices may hold the potential for providing a greater range of accommodation, they represent a radical departure from the natural lens structure of the eye.

While accommodating IOL devices hold the promise of more fully restoring the natural range of vision for cataract patients, they still fail to substantially mimic the eye's natural mechanism of accommodation. This is primarily because they rely solely on the eye's ciliary muscles to provide the accommodation and fail to respond to other forces which influence the natural accommodative process.

BRIEF SUMMARY

Preferred embodiments of the accommodating intraocular lens (IOL) devices disclosed herein substantially mimic the eye's natural mechanism of accommodation by responding not only to the contraction/relaxation of the ciliary muscles but also to the influence of the viscous body, which bulges forward and exerts a force anteriorly to change the curvature of the lens capsule. Thus, by providing both bilateral displacement and changes in curvature, the accommodating IOL devices disclosed herein provide broader range of accommodation that approximates that found in the natural eye.

In one embodiment, an accommodating IOL device adapted for implantation in the lens capsule of a subject's eye is described. The accommodating IOL device comprises an anterior portion having a refractive optical element, an elastic posterior portion; and an enclosed cavity defined between the anterior and posterior portions. The enclosed cavity is configured to contain a volume of fluid to space apart the anterior and posterior portions. The posterior portion is configured to contact the posterior portion of the lens bag (prior to shrinkage of the lens capsule following implantation) which in turn contacts the vitreous body at least in the area at and surrounding the optical axis when the IOL device is implanted in the eye and the cavity contains the fluid. The posterior portion actuates in response to an anterior force exerted by the vitreous body, causing the fluid to exert a deforming or displacing force on the refractive optical element.

In accordance with a first aspect of this embodiment, the refractive optical element increases its degree of curvature in response to the anterior force and decreases its degree of curvature in the absence of the anterior force.

In accordance with a second aspect of this embodiment, the refractive optical element is resiliently biased to having a degree of curvature that is substantially equal to the degree of curvature of the anterior portion of the subject's natural lens capsule.

In accordance with a third aspect of this embodiment, the IOL device is biased to a configuration having a width that is substantially equal to the width of the unaccommodated natural lens capsule along the optical axis.

In accordance with a fourth aspect of this embodiment, the IOL device has an equatorial diameter that is substantially equal to the equatorial diameter of the subject's natural lens capsule in the unaccommodated state.

In accordance with a fifth aspect of this embodiment, the anterior portion is dimensioned to engage the zonules when the IOL device is implanted in the subject's eye.

In accordance with a sixth aspect of this embodiment, the IOL device further comprises a haptic system coupled to the anterior portion. The haptic system may be configured to substantially center the refractive optical element in the path of the optical axis when implanted in the subject's eye. Alternatively or additionally, the haptic system is configured to bilaterally displace the refractive optical element along the optical axis in response to the contraction and relaxation of the ciliary muscles when the IOL device is implanted in the subject's eye.

In accordance with a seventh aspect of this embodiment, the volume of fluid contained in the cavity is sufficient to space apart the anterior and posterior portions at a distance $d_3$ along the optical axis that is substantially equal to the width of the subject's natural lens capsule along the optical axis $d_2$ in the unaccommodated state.

In another embodiment, an accommodating IOL device adapted for implantation in the lens capsule of a subject's eye is described. The accommodating IOL device comprises an anterior refractive optical element and a membrane comprising a posterior surface. The membrane is coupled to the anterior optical element and defines an enclosed cavity configured to contain a volume of fluid. The posterior portion is configured to contact the posterior portion of the lens capsule which in turn contacts the vitreous body at least in an area at and surrounding the optical axis when the IOL device is implanted in the eye and the cavity contains the fluid. The fluid deforms the anterior refractive optical element in response to an anterior force exerted on the posterior surface by the vitreous body.

In accordance with a first aspect of this embodiment, the anterior optical element further comprises a self-sealing valve to permit the injection of the fluid.

In accordance with a second aspect of this embodiment, the fluid is viscoelastic.

In accordance with a third aspect of this embodiment, the fluid is an aqueous solution of saline or hyaluronic acid.

In accordance with a fourth aspect of this embodiment, the fluid has substantially the same viscosity as the vitreous humor.

In accordance with a fifth aspect of this embodiment, the fluid has substantially the same refractive index as the aqueous humor or the vitreous humor.

In accordance with a sixth aspect of this embodiment, the membrane is coupled to the anterior refractive optical element about its periphery.

In accordance with a seventh aspect of this embodiment, the anterior refractive optical element is contained within the enclosed cavity of the membrane.

In accordance with a eighth aspect of this embodiment, the posterior portion further comprises a reinforced portion.

In a further embodiment, a method for implanting an accommodating intraocular accommodating lens (IOL) device in a subject's eye is described. The method comprises introducing an IOL device in the lens capsule of the subject's eye through an incision in the subject's eye, wherein the IOL device comprises a refractive optical element coupled to an elastic membrane to define an internal cavity; positioning the IOL device within the lens capsule of the subject's eye to substantially center the refractive optical element along an optical axis; and injecting a volume of fluid into the internal cavity of the IOL device sufficient to cause the elastic membrane to contact the posterior portion of the lens capsule which in turn contacts the vitreous body in at least an area at and surrounding the optical axis.

Other objects, features and advantages of the described preferred embodiments will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

Preferred and non-limiting embodiments of the invention may be more readily understood by referring to the accompanying drawings in which.

Like numerals refer to like parts throughout the several views of the drawings.

DETAILED DESCRIPTION OF THE PREFERRED EMBODIMENTS

Specific, non-limiting embodiments of the present invention will now be described with reference to the drawings. It should be understood that such embodiments are by way of example only and merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

Figure 1A:
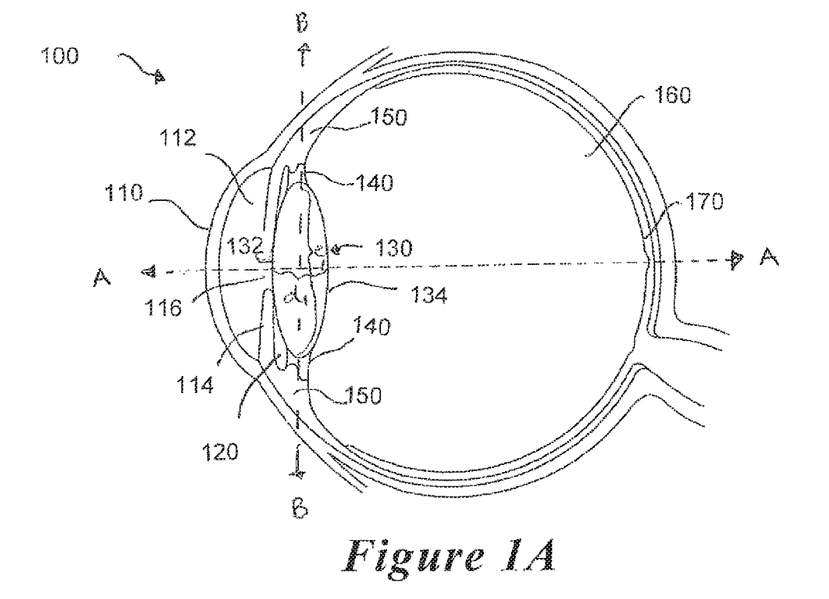
FIGS. 1A and B are sectional views illustrating the certain anatomical features of the human eye with the lens in the unaccommodated and accommodated states, respectively.
Figure 1B:
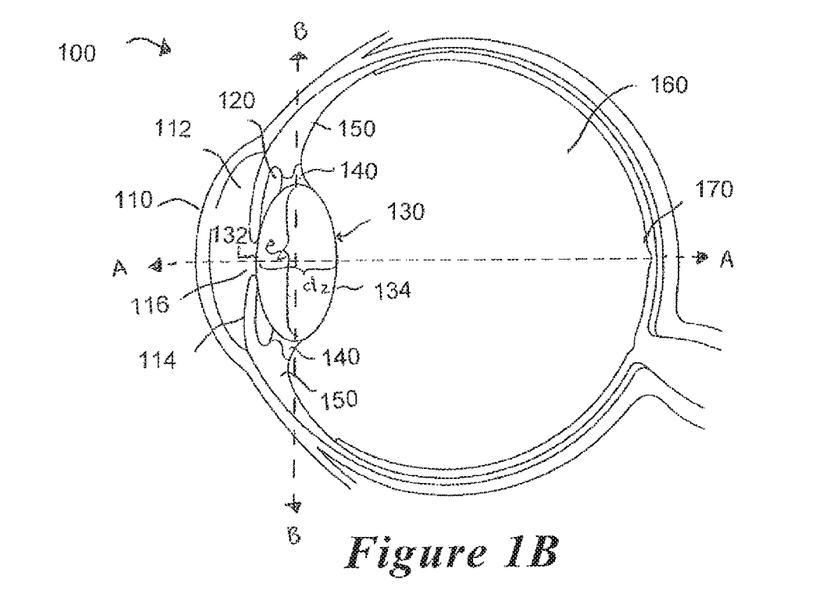

As shown in FIGS. 1A-B, the human eye 100 comprises three chambers of fluid: the anterior chamber 112, the posterior chamber 120 and the vitreous chamber 160. The anterior chamber 112 corresponds generally to the space between the cornea 110 and the iris 114 and the posterior chamber 120 corresponds generally to the space bounded by the iris 114, the lens 130 and zonule fibers 140 connected to the periphery of the lens 130. The anterior chamber 112 and the posterior chamber 120 contain a fluid known as the aqueous humor, which flows therebetween through an opening that is defined by the iris 114, known as the pupil 116. Light enters the eye 100 through the pupil 116 and travels along a visual axis A-A, striking the retina 170 and thereby produce vision. The iris 114 regulates the amount of light entering the eye 100 by controlling the size of the pupil 116.

The vitreous chamber 160 is located between the lens 130 and the retina 170 and contains another fluid, known as the vitreous humor. The vitreous humor is much more viscous than the aqueous humor and is a transparent, colorless, gelatinous mass. Although much of the volume of the vitreous humor is water, it also contains cells, salts, sugars, vitrosin (a type of collagen), a network of collagen type II fibers with the glycosaminoglycan hyaluronic acid, and proteins. The vitreous has a viscosity two to four times that of pure water, giving it a gelatinous consistency. It also has a refractive index of 1.336.

Unlike the aqueous humor contained in the anterior and posterior chambers 112, 120 of the eye, which is continuously replenished, the vitreous humor is stagnant. The vitreous often becomes less viscous and may even collapse as part of the aging process. It is believed that the collagen fibers of the vitreous humor are held apart by electrical charges. With aging, these charges tend to reduce, and the fibers may clump together. Similarly, the vitreous humor may liquefy, a condition known as syneresis, allowing cells and other organic clusters to float freely within the vitreous humor. These allow floaters which are perceived in the visual field as spots or fibrous strands.

The lens 130 is a clear, crystalline protein membrane-like structure that is quite elastic, a quality that keeps it under constant tension via the attached zonules 140 and ciliary muscles 150. As a result, the lens 130 naturally tends towards a rounder configuration, a shape it must assume for the eye 100 to focus at a near distance as shown in FIG. 1B. By changing shape, the lens functions to change the focus distance of the eye so that it can focus on objects at various distances, thus allowing a real image of the object of interest to be formed on the retina.

As shown in FIGS. 1A and 1B, the lens 130 may be characterized as a capsule having two surfaces: an anterior surface 132 and a posterior surface 134. The anterior surface 132 faces the posterior chamber 120 and the posterior surface 134 faces the vitreous body 160. The posterior surface 134 contacts the vitreous body 160 in such a manner that fluid movements within the vitreous body 160 are communicated to the posterior surface 134 and may cause the shape of the lens 130 to change.

The eye's natural mechanism of accommodation is reflected by the changes in shape of the lens 130 and thus the extent to which it refracts light.

FIG. 1A shows the eye 100 in a relatively unaccommodated state, as may be the case when the eye is focusing at a distance. In an unaccommodated state, the ciliary muscles 150 relax, thereby increasing the diameter of its opening and causing the zonules to be pulled away from the visual axis A-A. This, in turn, causes the zonules 140 to radially pull on the periphery of the lens 130 and cause the lens 130 to flatten. As the shape of the lens 130 is flattened, its ability to bend or refract light entering the pupil is reduced. Thus, in an unaccommodated state, the lens 130 has a flatter surface, its diameter $e_1$ along the equatorial axis B-B is lengthened and its thickness $d_1$ along the visual axis A-A is decreased, all relative to the accommodated state (compare $e_2$ and $d_2$ in FIG. 1A).

FIG. 1B shows the eye 100 in a relatively accommodated state, as may be the case when the eye is focusing on a nearby object. In an accommodated state, the ciliary muscles 150 contract, and the contraction of the ciliary muscles 150 causes them to move in an anterior direction. This, in turn, reduces the stress on the zonules 140, thereby lessening the stress exerted by the zonules 140 on the lens 130. The lens 130 thereupon undergoes elastic recovery and rebounds to a more relaxed and accommodated state, in which the lens 130 has a more convex anterior surface, its diameter $e_2$ along the equatorial axis B-B is decreased and its thickness $a'_2$ along the visual axis A-A is increased relative to the unaccommodated state (compare $e_2$ and $d_1$ in FIG. 1A). Although FIG. 1B depicts the anterior and posterior surfaces 132, 134 of the lens capsule 130 as having roughly the same radius of curvature, it is believed that during accommodation, the radius of curvature for the anterior surface 132 increases and the radius of curvature of the posterior surface 134 is not significantly changed from its unaccommodated state.

As demonstrated by FIGS. 1A and 1B, accommodation results from the changes in shape of the lens 130, including the changes in the thickness of the lens capsule 130 ($d_1$ vs. $d_2$), changes in the diameter of the lens capsule 130 ($e_1$ vs. $e_2$) and the changes in the curvature of the anterior surface 132 of the lens capsule 130. While the ciliary muscles 150 are known to play a significant role in exerting these changes, it is believed that the vitreous body 160 also plays a significant role, primarily due to the nature of the contact between the posterior surface 134 of the lens 130 and the vitreous body 160, in which the posterior surface 134 responds to and transmits anterior fluid movement in the vitreous body 160 to effectuate changes in shape of the lens 130.

Figure 2A:
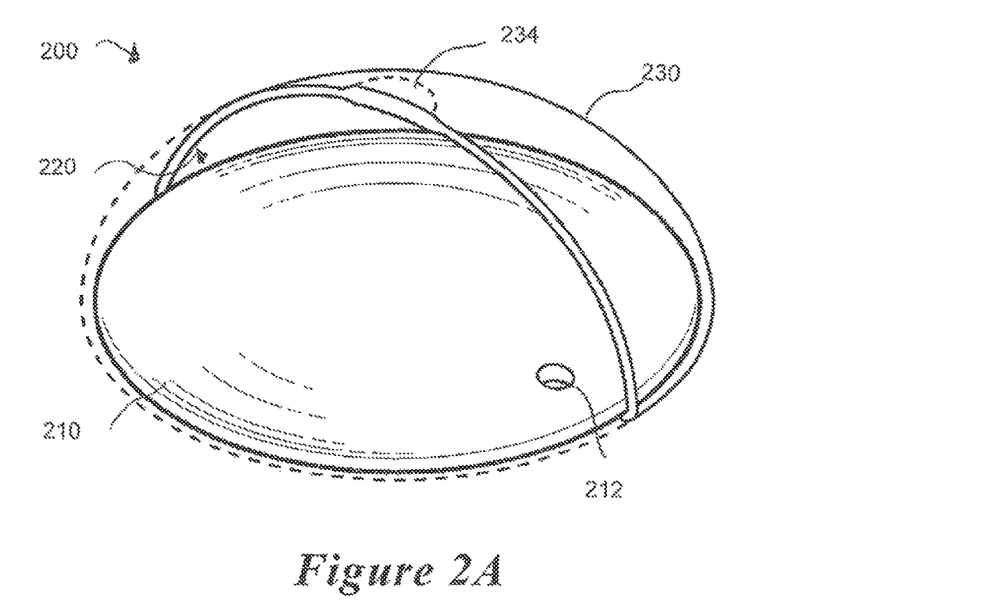
FIGS. 2A, B and C are cut-away perspective, plan and cross-sectional views, respectively, of an embodiment of a refractive optical element coupled to a fluid-filled lens capsule.
Figure 2B:
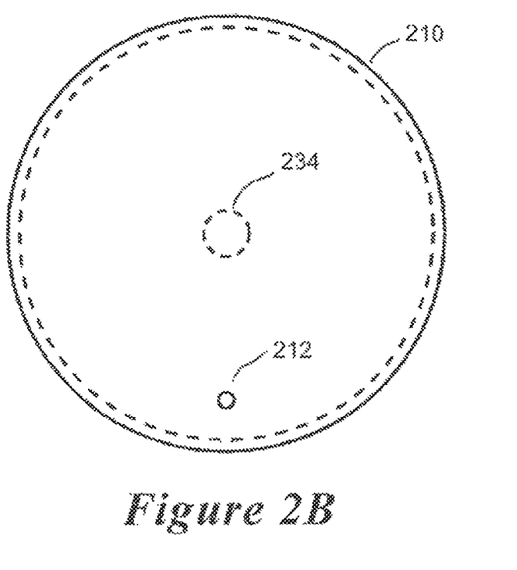
Figure 2C:
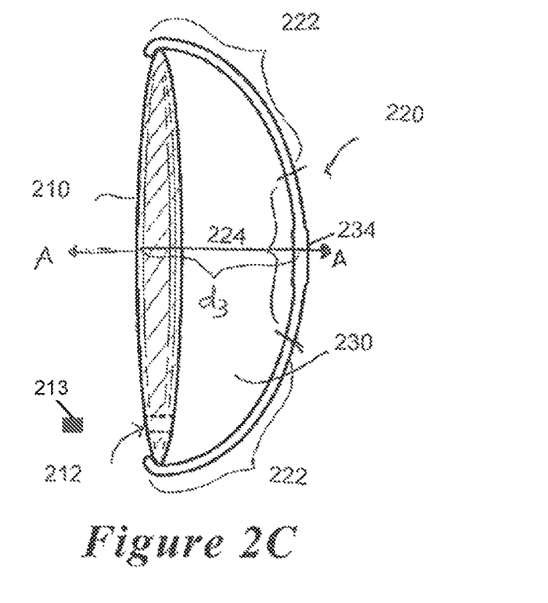

FIGS. 2A-C illustrate an embodiment of an accommodating IOL device 200 that may be implanted into the lens capsule 130 of the eye following cataract removal. The IOL device 200 is shown to comprise an optical element 210 and a flexible membrane 230 coupled to the optical element 210. The optical element 210 and the flexible membrane 230 together define an interior cavity 220 which may be filled with fluid. The optical element 210 may further optionally comprise an injection port 212 to permit the injection of the fluid to fill the cavity 220. In a preferred embodiment, the injection port 212 comprises a one-way value and is self-sealing. In another preferred embodiment, a separate plug 213 may be provided to seal off the injection port 212. While FIGS. 2-7 depict the injection port 212 as being located within the optical element 210, it is understood that the placement of the injection port 212 is not critical, so long as its placement does not impede vision.

The optical element 210 may be made of plastic, silicone, acrylic, or a combination thereof. In accordance with a preferred embodiment, the optical element 210 is made of poly(methyl methacrylate) (PMMA), which is a transparent thermoplastic, sometimes called acrylic glass. Because the optical element 210 is responsible for providing most, if not substantially all, of the refractive power of the IOC device, the optical element 210 is preferably sufficiently flexible so as to change its curvature in response to the contraction/relaxation of the anterior force that is exerted when the vitreous body bulges in the anterior direction.

In accordance with one embodiment, the optical element 210 is resiliently biased to a shape that approximates the shape of a natural and unaccommodated lens (see FIG. 1A). The optical element 210 accordingly increases its degree of curvature in response to the anterior force exerted by the vitreous body and is resiliently biased to a flatter configuration or a decreased degree of curvature, similar to the configuration of the natural lens in the unaccommodated state, in the absence of the anterior force.

In accordance with another embodiment, the optical element 210 is resiliently biased to a shape that approximates the shape of a natural and accommodated lens (see FIG. 1B). The optical element 210 accordingly is resiliently biased to a convex configuration similar to that of the natural lens in the accommodated state and assumes a less convex configuration as the ciliary muscles 150 relax and the tension of the zonules 140 on the lens capsule 130 increases.

In the embodiment shown in FIGS. 2A-C, the optical element 210 has a disk shape of sufficient diameter to engage the zonules 140 of the eye. As this dimension may differ from patient to patient, it is contemplated that the optical element 210 be provided in a range of sizes to fit a patient's anatomy. In other embodiments, the optical element 210 may further comprise a separate haptic system (FIGS. 3-6) to engage the zonules 140 of the eye. In these embodiments, the optical element 210 may have a diameter that is significantly smaller than the embodiments in which the optical element 210 directly engages the zonules 140 of the eye.

Regardless, in engaging the zonules 140, the IOL device responds to part of the accommodative mechanism of the eye in which the ciliary muscles 150 and the zonules 140 cause a bilateral movement of the optical element 210 along the optical axis to thereby provide part of the accommodating response.

The accommodating IOL device 200 is additionally configured to allow the optical element 210 change its shape in response to the forces exerted upon it by the vitreous body 160. This is achieved by providing a flexible optical element 210 and a fluid-filled flexible membrane 230 that is configured to transmit the anterior force of the vitreous body 160 during accommodation to affect the changes in the shape of the lens capsule 130. Preferably, in order to effectuate the transfer of the anterior movements of the vitreous body 160 upon the lens capsule 130, the membrane 230 contacts a substantial area of the posterior surface 134 of the lens capsule 130 and the membrane is sufficiently flexible and substantially devoid of any rigid material that would prevent it from responding to the anterior movements of the vitreous body 160. Thus, the accommodating IOL device 200 is distinguishable from prior art dual lens IOL devices in maintaining a flexible boundary between the lens capsule 130 and the vitreous body 160. In a particularly preferred embodiment, the membrane 230 is sufficiently thin and deformable so as not to impede the natural flexible boundary between the lens capsule 130 and the vitreous body 160.

Moreover, as explained above, there is a degree of shrinkage experienced by the lens capsule 130 after cataract surgery which depends on the profile and the dimension of the IOL device that is implanted in the lens capsule 130. As many of the prior art devices have a profile and/or dimension that is substantially different from the original lens capsule 130 (e.g., by having a smaller width d along the optical axis A-A or a smaller diameter along the equatorial axis B-B), a degree of shrinkage is expected which, in turn, affects the extent to which the lens capsule 130 is engaged to the vitreous body 160. In one preferred embodiment, the IOL device minimizes the degree to which this shrinkage occurs by significantly engaging the contours of the lens capsule 130, particularly the posterior surface 134 of the lens capsule 130 via the fluid filled cavity 220 defined by the optical element 210 and membrane 230. The membrane 230 is preferably configured to contact a substantial, if not substantially all, of the posterior surface 134 of the lens capsule 130 at implantation and before any significant shrinkage of the lens capsule 130 has occurred.

As explained above with respect to FIGS. 1A-B, during accommodation, the vitreous body 160 exerts a force in the anterior direction along the optical axis A-A and pushes the lens capsule 130 in the anterior direction. This, in turn, causes the anterior surface 132 of the lens capsule 130 to become more curved and thus to further refract the light.

Because the optical element 210 is responsible for providing most, if not substantially all, of the refractive power of the IOC device, the optical element 210 is preferably sufficiently flexible so as to change its curvature in response to the contraction/relaxation of the anterior force that is exerted when the vitreous body bulges in the anterior direction. In a preferred embodiment, the optical element 210 is resiliently biased to a shape that approximates the shape of a natural and unaccommodated lens (see FIG. 1A). The optical element 210 accordingly increases its degree of curvature response to the anterior force exerted by the vitreous body and is resiliently biased to a flatter configuration or a decreased degree of curvature, similar to the configuration of the natural lens in the unaccommodated state, in the absence of the anterior force.

The flexible membrane 230 may be constructed from any biocompatible elastomeric material. In a preferred embodiment, the flexible membrane 230 has an external surface that approximates the posterior surface of the lens capsule adjacent the vitreous body. The flexible membrane 230 is preferably configured and shaped to contact a substantial, if not the entire, area of the posterior surface of the lens capsule. In a particularly preferred embodiment, this point of contact is at and around the optical axis of the posterior surface.

The flexible membrane 230 is preferably configured to maximize this transfer of force from the vitreous body to the lens 122. As shown in FIGS. 1A and 1B, the anterior portion 132 of the lens 130 of the unaccommodated eye 100 in FIG. 1A has a lesser degree of curvature (i.e., is flatter) than that of the accommodated eye 100 of FIG. 1B. As the vitreous body is believed to exert an anterior force along the optical axis on the lens 122 to effectuate a greater degree of curvature, it is preferable to maximize transfer of force resulting from anterior vitreous movement onto the lens 122.

In accordance with one preferred embodiment, the flexible membrane 230 may have areas of greater and lesser elasticity so as to maximize the translation of the anterior movements of the vitreous body. For example, as shown in FIG. 2C, the flexible membrane 230 may comprise a central posterior portion 224 (corresponding to an area surrounding the optical axis A-A when the IOL device 200 is implanted) having greater elasticity than the adjacent circumferential portion 222. Having areas of reduced elasticity in the adjacent circumferential portion 222 may reduce radial expansion of the membrane 230 and allow the anterior force exerted by the vitreous body 170 to be more effectively translated and applied onto the optical element 210 by the fluid contained in the cavity 220 to thereby increase the curvature of the optical element 210.

In accordance with another preferred embodiment, the IOL device 200 may be configured to resiliently assume a shape having a width $d_3$ that is substantially equal to the width the lens capsule 130 accommodated eye (see $d_2$ of FIG. 1B) when it is implanted in the patient's eye. This may be achieved by constructing the IOL device 200 with resilient materials having some degree of shape memory and also by filling the cavity 220 with a volume of fluid sufficient to expand the flexible membrane 230 to the desired width, $d_3$.

In accordance with a further preferred embodiment, the IOL device 200 comprises a single lens. The incorporation of additional lenses in the IOL device would likely interfere with the ability of the lens to deform (i.e., increase its curvature and provide additional diopters of power) to anterior vitreous movement.

The flexible membrane may preferably be made from a polyvinylidene fluoride (PDVF) material. PDVF is believed to allow for the transmission of lasers energy without, itself, becoming degraded. Optionally, a reinforced portion 234 of the flexible membrane 230 may optionally be provided to resist degradation upon the application of lasers of various wavelengths. In a preferred embodiment, the reinforced section 234 is positioned at an area on the membrane 230 corresponding to the optical axis A-A when the IOL device 200 is implanted in the subject's eye. Normally, after cataract surgery, a few of the residual epithelial cells in the lens capsule may migrate to a posterior surface of the bag resulting in various degrees of fibrosis which, in turn, may lead to undesired posterior capsule opacification (PCO). PCO is undesired, particularly at the optical path, and is typically treated by the application of laser pulses (e.g., YAG laser capsulotomy) to burn away the fibrotic membrane. Thus, a reinforced portion 234 may be provided on the membrane 230 as a protective mechanism against the potentially degradative effects of laser treatment on the membrane 230. In a preferred embodiment, the reinforced portion 234 remains flexible and is sized to correspond to the central area at and surrounding the optical axis A-A.

Once the IOL device is implanted in the lens capsule of the patient, a volume of fluid is injected into the cavity 220 via an injection port 212. In a preferred embodiment, the fluid is an aqueous solution of saline or hyaluronic acid and does not provide a significant, or any, contribution to the refractive power of the IOC device. Thus, the function of the fluid is primarily as a vehicle to transfer force resulting from the movement of the vitreous body 150 onto the optical element 210 to provide the accommodation. In a preferred embodiment, the fluid has a viscosity that is substantially the same as the vitreous humor. In another preferred embodiment, the fluid has a refractive index that is substantially the same as the aqueous humor or the vitreous humor.

The IOL device is distinguishable from prior art teachings in which the lens capsule is with various types of polymers, which are injected in liquid form and set with UV or other methods of polymerization. These at have been met with much difficulty as it is often difficult to control the refractive power provided by the polymerized polymers. Here, the refractive power is provided substantially, if not entirely, by the optical element 210 and the fluid that is contained within the cavity 220 does not contribute significantly, if at all, to providing the refractive power of the IOL device. Moreover, unlike the prior art polymers used to fill the lens capsule, the fluid is a relatively inert or biocompatible material, such as saline, or it alternatively contains a high molecular weight compound, such as hyaluronic acid, which does not readily leak from the IOL device 200.

The precise volume of fluid injected into the cavity 220 may differ based on the subject's anatomy, among other factors. The volume of fluid injected into the cavity 220 is not critical so long as it is sufficient to expand the membrane 230 such that the posterior portion of the membrane 230 substantially contacts the posterior portion of the lens capsule and engages the vitreous body of the subject's eye. As explained above, in one preferred embodiment, a volume of fluid is injected into the cavity 220 so as to provide a width $d_3$ of the IOL device along the optical axis A-A substantially approximating the lens width $d_2$ of the accommodated eye 100. In another preferred embodiment, a volume of fluid is injected into the cavity 220 so as to provide a width $d_3$ of the IOL device along the optical axis AA substantially approximating the width $d_1$ of the unaccommodated eye 100.

A haptic system may be incorporated with the IOL device to position the optical element 210 at the optical axis A-A when implanted in the subject's eye. As it is preferable to center the optical element 210 relative to the optical axis A-A, the haptic system preferably comprises a plurality of haptic members extending radially from the IOL device and engaging the zonules 140 surrounding the lens capsule 130 of the eye.

Figure 3A:
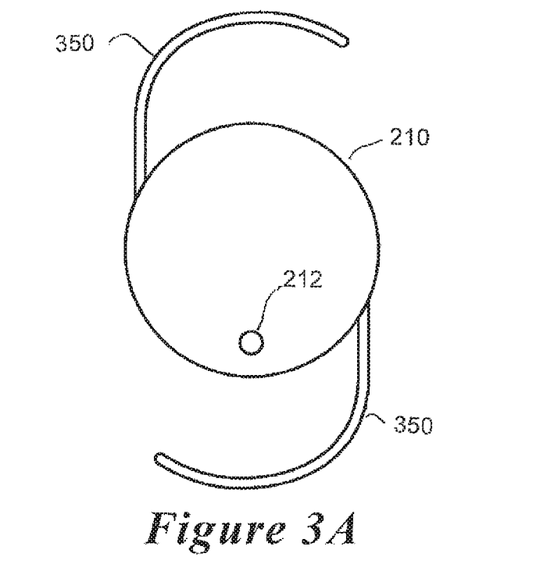
FIGS. 3A and B are plan and side views, respectively, of an embodiment of a refractive optical element and haptic system.
Figure 3B:
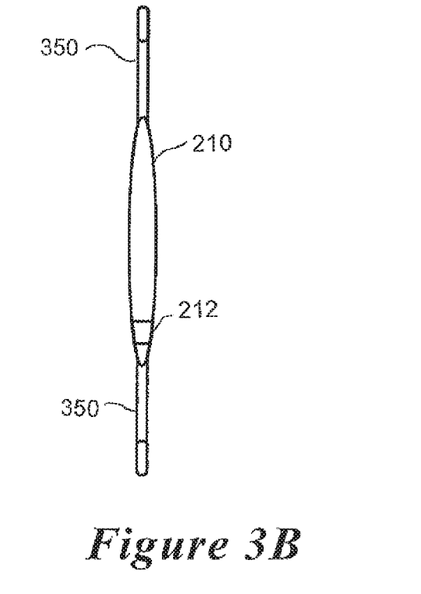

FIGS. 3A-B depict an optical element 210 comprising a pair of spring haptics 350 coupled to opposing sides of the optical element 210. As further shown in FIGS. 4A-C, a flexible membrane 230 may be coupled to the optical element 210/haptic 350 assembly along the periphery of the optical element 210. A seal is effectuated between the flexible membrane 230 and the periphery of the optical element 210 by laser welding and any other means known to those of skill in the art.

Figure 4A:
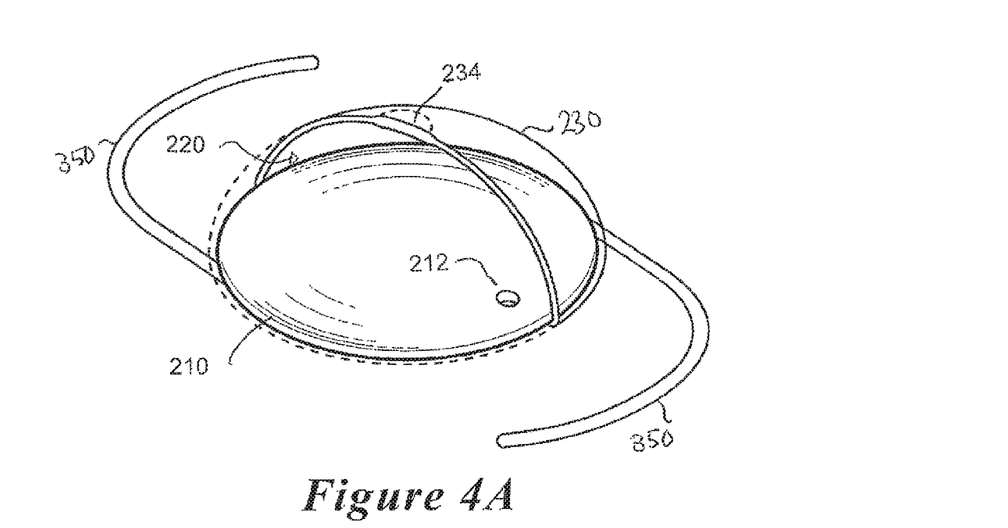
FIGS. 4A, B and C are cut-away perspective, plan and cross-sectional views, respectively, of an embodiment of a refractive optical element and haptic system of FIGS. 3A-B coupled to a fluid filled lens capsule.
Figure 4B:
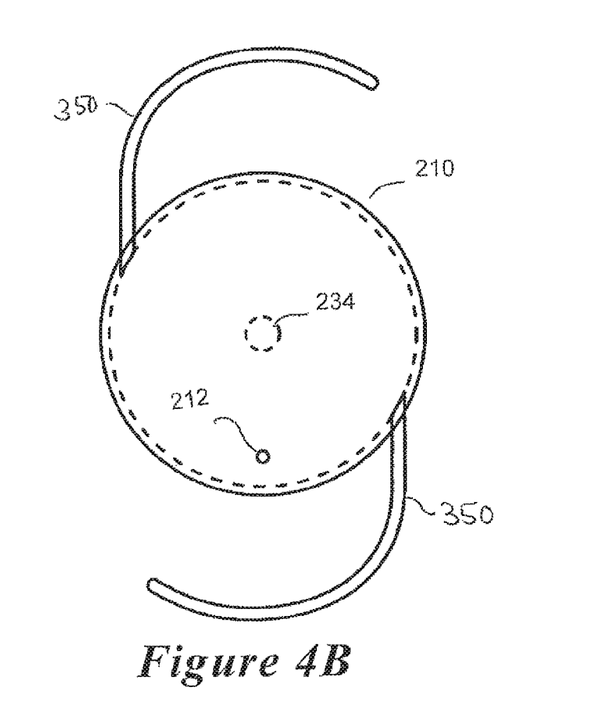
Figure 4C:
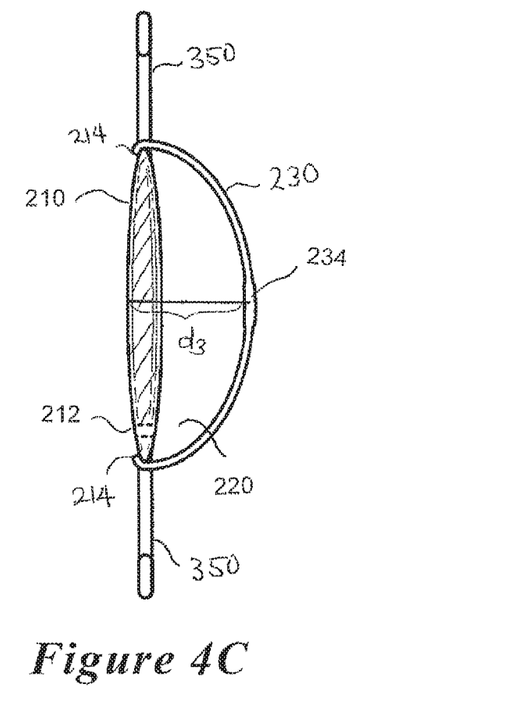

In another embodiment, the optical element 210 may be contained within a flexible membrane 230 that fully encloses the optical element 210. In accordance with this element, flexible membrane 230 has a bag or balloon-like configuration and the spring haptics 350 may be attached either (1) to the optical element 210 itself and protrude from a sealed opening in the flexible membrane 230 or (2) to the flexible membrane 230. Although FIGS. 3-4 depict a pair of spring haptics 350 extending radially from the optical element 210, it is understood that any number of spring haptics 350 may be provided so long as optical element 210 is centered about the optical axis A-A when the IOL device is implanted in the eye.

Figure 5A:
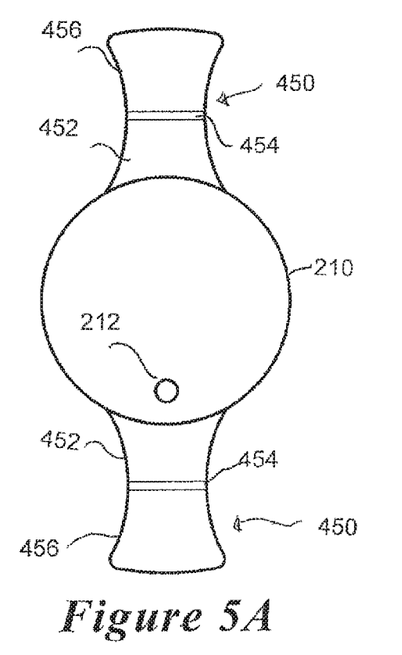
FIGS. 5A and B are plan and side views, respectively, of another embodiment of a refractive optical element and haptic system.
Figure 5B:
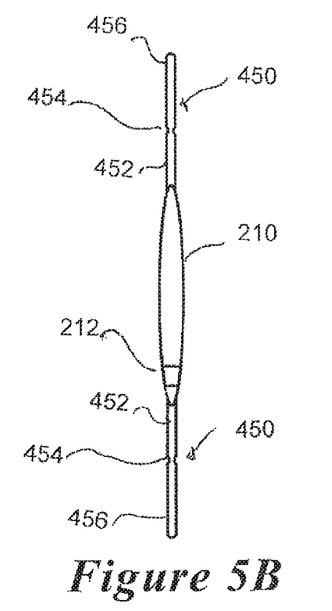

FIGS. 5A-B depict an optical element 210 comprising a pair of plate haptics 450 coupled to opposing sides of the optical element 210. The plate haptics 450 comprise a pair of plate members each comprising a first end 452 attached to the optical element 210 and a second end 456 configured to engage the zonules 140 of the eye 100 when implanted in the lens capsule 130. A hinge 454 is disposed between the first and second ends 452, 456, to allow lateral movement of the optical element 210 in the anterior and posterior directions as the ciliary muscles 150 relax and contract, respectively. As further shown in FIGS. 6A-C, a flexible membrane 230 may he coupled to the optical element 210/haptic 450 assembly along the periphery of the optical element 210.

Figure 6A:
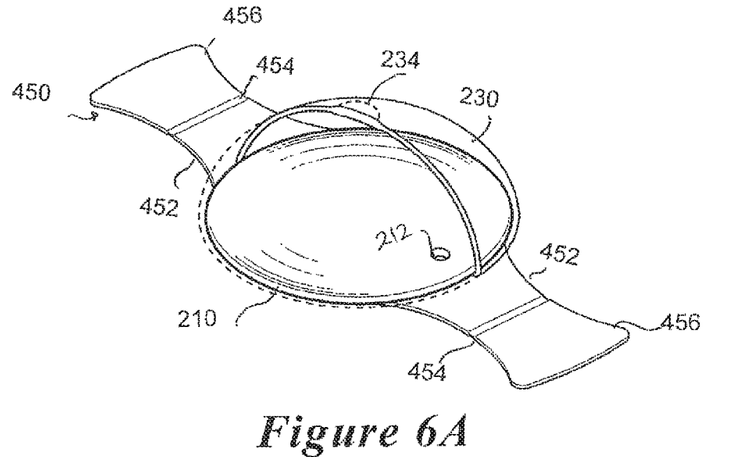
FIGS. 6A, B and C are cut-away perspective, plan and cross-sectional views, respectively, of another embodiment of a refractive optical element and haptic system of FIGS. 5A-B coupled to a fluid-filled lens capsule.
Figure 6B:
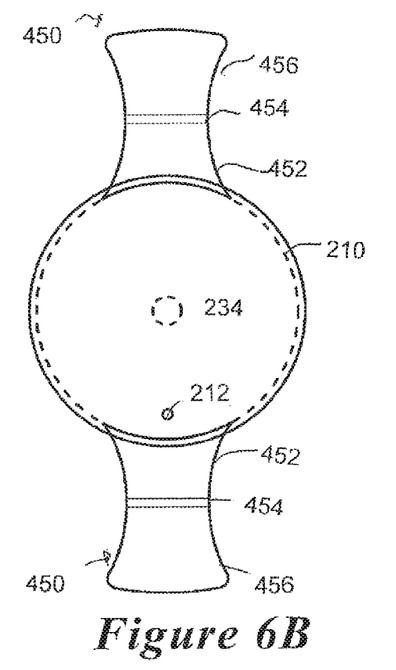
Figure 6C:
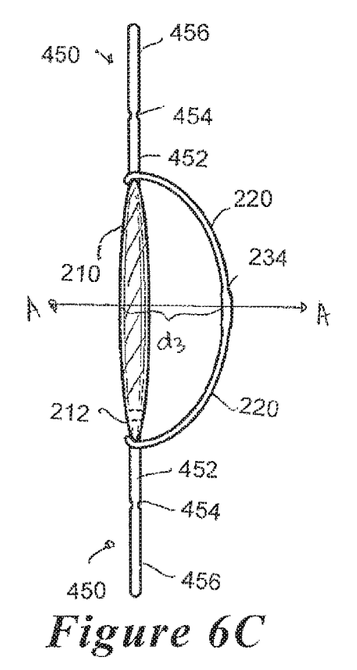

In another embodiment, the optical element 210 may be contained within a flexible membrane 230 that fully encloses the optical element 210. In accordance with this element, the spring haptics 450 may be attached either (1) to the optical element 210 itself and protrude from a sealed opening in the flexible membrane 230 or (2) to the flexible membrane 230. Although FIGS. 5-6 depict a pair of plate haptics 450 extending radially from the optical element 210, it is understood that any number of plate haptics 450 may be provided so long as optical element 210 is centered about the optical axis A-A when the IOL device is implanted in the eye.

Figure 7:
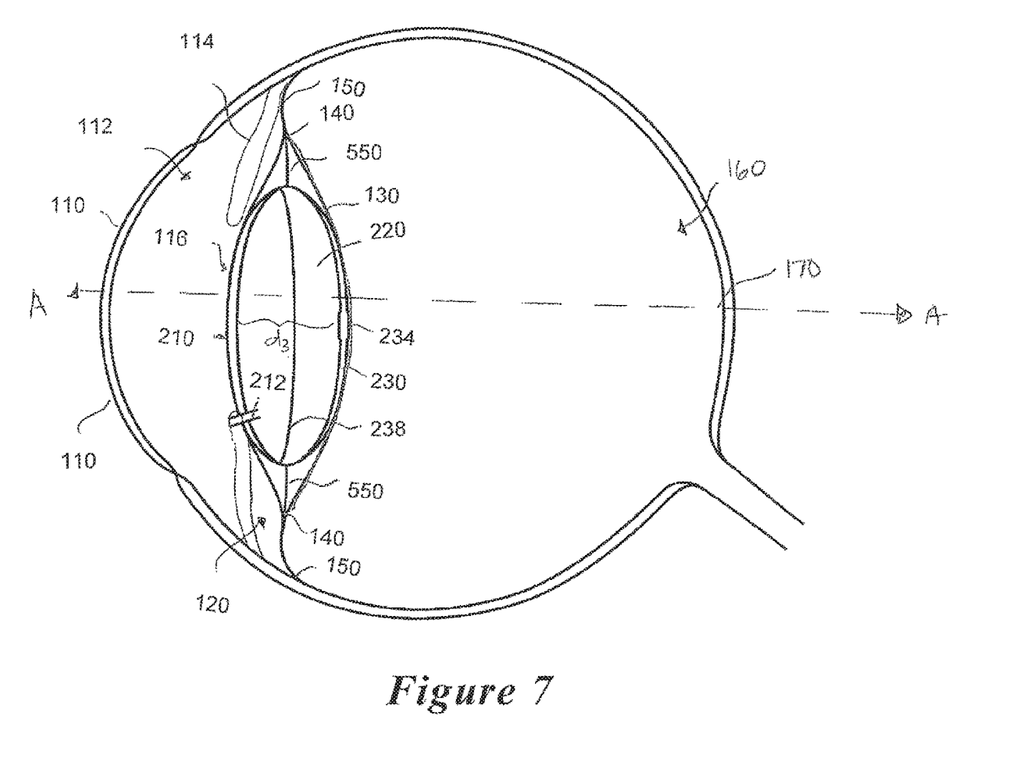
FIG. 7 depicts an embodiment of the intraocular lens device implanted in the posterior chamber of a human eye.

FIG. 7 depicts an embodiment of the accommodating IOL device implanted in the lens capsule 130 of the eye in an accommodated state. Because both the optical element 210 and the membrane 230 of the IOL device 200 is sufficiently flexible, it may be folded or rolled compactly prior to implantation, thereby requiring only a small incision of a few millimeters for insertion into the eye. As shown in FIG. 7, after the IOL device is implanted and the cavity 220 is filled with fluid, the IOL device is divided roughly in two: the anterior lens portion 210 facing the posterior capsule 120 and the posterior membrane portion 230 facing the vitreous body 160. The width $d_3$ of the IOL device is resiliently biased to having a width that is roughly equal to the width of the natural lens capsule when it is in an accommodated state (see $d_2$ of FIG. 1B). The posterior membrane portion 230 has an area of contact that approximates the surface area of the posterior portion 134 of the lens capsule 130 (See FIGS. 1A-B). Two or more haptics 550 are shown to protrude from the IOL device to substantially center the anterior lens portion 210 along the optical axis A-A.

The accommodated IOL device shown in FIG. 7 is implanted in the lens capsule of a subject's eye by introducing an IOL device in the lens capsule of the subject's eye through a small incision in the subject's eye, wherein the IOL device comprises a refractive optical element 210 coupled to an elastic membrane 230 to define an internal cavity 220. The IOL device is then positioned within the lens capsule 130 of the subject's eye to substantially center the refractive optical element 210 along an optical axis A-A. A volume of fluid is then injected into the internal cavity 220 of the IOL device sufficient to cause the elastic membrane 230 to contact the posterior portion of the lens capsule which, in turn, contacts the vitreous body in at least an area at and surrounding the optical axis A-A. In a preferred embodiment, the volume of fluid injected into the internal cavity 220 is sufficient to produce a width $d_3$ of the IOL device along the optical axis A-A that is substantially equal to the width of a natural lens capsule in an accommodated state.

The invention described and claimed herein is not to be limited in scope by the specific preferred embodiments disclosed herein, as these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

What is claimed is:

1. An accommodating intraocular lens (IOL) device adapted for implantation in a lens capsule of a subject's eye, the IOL device comprising:
    an anterior biconvex lens;
    an elastic posterior portion;
    an enclosed cavity defined between a posterior surface of the anterior biconvex lens and the elastic posterior portion;
    a plate haptic coupled to a periphery of the elastic posterior portion and a periphery of the anterior biconvex lens, the haptic having a flat anterior surface and a flat posterior surface, a central plane of the plate haptic being aligned coplanar with a central plane of the anterior biconvex lens, the plate haptic comprising a hinge disposed between an outer end of the plate haptic and the periphery of the anterior biconvex lens that is configured to facilitate anterior and posterior axial movement of the anterior biconvex lens; and
    an injection port disposed through a periphery of the accommodating IOL;
    wherein the injection port is configured to be closed to contain a volume of fluid within the enclosed cavity to space apart the anterior biconvex lens and elastic posterior portion;
    wherein the elastic posterior portion is configured to contact a posterior area of the lens capsule adjoining a vitreous body at least in an area at and surrounding an optical axis of the subject when the IOL device is implanted in the eye and the enclosed cavity contains the volume of fluid; and
    wherein the posterior elastic portion actuates in response to an anterior force exerted by the vitreous body, causing the volume of fluid to exert a deforming and displacing force on the anterior biconvex lens.

2. The accommodating IOL device of claim 1, wherein the anterior biconvex lens increases a degree of curvature in response to the anterior force exerted by the vitreous and decreases the degree of curvature in the absence of the anterior force.

3. The accommodating IOL device of claim 1, the plate haptic comprising a narrowed portion between the outer end of the plate haptic and the periphery of the anterior biconvex lens.

4. The accommodating IOL device of claim 3, wherein the plate haptic is configured to substantially center the anterior biconvex lens optical in a path of the optical axis of the subject when implanted in the subject's eye.

5. The accommodating IOL device of claim 4, wherein the plate haptic is configured to bilaterally displace the anterior biconvex lens along the optical axis of the subject in response to a contraction and relaxation of a subject's ciliary muscles when the IOL device is implanted in the subject's eye.

6. The accommodating IOL device of claim 1, wherein the injection port is configured to receive a plug to close the volume of fluid within the enclosed cavity.

7. An accommodating intraocular lens (IOL) device adapted for implantation in a lens capsule of a subject's eye, the IOL device comprising:
    an anterior biconvex lens;
    an elastic portion coupled to the anterior biconvex lens;
    an enclosed cavity defined between the anterior biconvex lens and the elastic portion;
    a haptic coupled to a periphery of the anterior biconvex lens, the haptic having a flat anterior surface and a flat posterior surface, a central plane of the haptic being aligned coplanar with a central plane of the anterior biconvex lens; and
    an injection port disposed through a periphery of the accommodating IOL that is configured to close
    to contain a volume of fluid within the enclosed cavity to space apart the anterior biconvex lens and the elastic portion;
    wherein when the elastic portion actuates in response to ocular force, the volume of fluid and the anterior biconvex lens shift in response to such actuation.

8. The IOL device of claim 7, wherein the injection port extends into the enclosed cavity and is self-sealing.

9. The IOL device of claim 7, wherein the haptic comprises:
    a first end directly coupled to the periphery of the anterior biconvex lens; and
    a second end that is configured to be compressed by ocular forces of the subject;
    wherein a hinge is disposed between the second end and the anterior biconvex lens such that the IOL device is configured to accommodate as ocular forces vary when ciliary muscles of the subject contract and relax.

10. The IOL device of claim 7, wherein the elastic portion comprises a flexible membrane.

11. The IOL device of claim 7, wherein the elastic portion comprises a central portion that is thicker than a peripheral thickness of the elastic portion, wherein central portion is configured to protect against the potentially degradative effects of laser treatment from YAG laser capsulotomy.

12. The IOL device of claim 7, wherein the haptic is solid, not having an internal cavity configured to contain a volume of fluid between the flat anterior surface and the flat posterior surface.

13. The IOL device of claim 7, wherein the haptic comprises a plate haptic.

14. The IOL device of claim 13, further comprising a second haptic configured to couple the IOL device with a capsular bag of the subject's eye.

15. The accommodating IOL device of claim 7, wherein the injection port is configured to receive a plug to close the volume of fluid within the enclosed cavity.

* * * * *